US010912914B2

(12) United States Patent
Bexson

(10) Patent No.: US 10,912,914 B2
(45) Date of Patent: Feb. 9, 2021

(54) SYSTEMS AND METHODS FOR BOTTLE RETENTION

(71) Applicant: GE Precision Healthcare LLC, Wauwatosa, WI (US)

(72) Inventor: Joe M. Bexson, Madison, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/433,895

(22) Filed: Jun. 6, 2019

(65) Prior Publication Data
US 2020/0384237 A1 Dec. 10, 2020

(51) Int. Cl.
A61M 16/18 (2006.01)

(52) U.S. Cl.
CPC ................................ A61M 16/183 (2013.01)

(58) Field of Classification Search
CPC .................................................. A61M 16/193
USPC ...... 141/383, 350, 351; 220/86.2; 296/97.22
See application file for complete search history.

(56) References Cited

U.S. PATENT DOCUMENTS

| 1,600,549 | A | | 9/1926 | Jurs |
| 2,145,758 | A | * | 1/1939 | Fellow ............... B60K 15/0406 220/822 |
| 2,202,459 | A | | 5/1940 | Link |
| 2,321,336 | A | * | 6/1943 | Tondreau .................. F16K 3/03 251/212 |
| 3,115,907 | A | | 12/1963 | Labat |
| 3,125,135 | A | | 3/1964 | Boyer et al. |
| 3,146,808 | A | | 9/1964 | Zellweger |
| 3,217,762 | A | | 11/1965 | Burchett |
| 3,277,674 | A | | 10/1966 | Klein et al. |
| 3,329,396 | A | * | 7/1967 | Heaton ................... C03B 7/088 251/212 |
| 3,416,577 | A | | 12/1968 | Franz |
| 3,799,222 | A | | 3/1974 | Franz |
| 3,874,380 | A | | 4/1975 | Baum |
| 4,614,437 | A | | 9/1986 | Buehler |
| 4,883,049 | A | | 11/1989 | McDonald |
| 4,893,659 | A | | 1/1990 | Loliger |
| 5,170,823 | A | | 12/1992 | Gregory et al. |
| 5,287,898 | A | | 2/1994 | Falb et al. |
| 5,293,913 | A | | 3/1994 | Preszler |
| 5,381,836 | A | | 1/1995 | Braatz et al. |
| 5,505,236 | A | | 4/1996 | Grabenkort et al. |
| 5,617,906 | A | | 4/1997 | Braatz et al. |
| 6,666,237 | B2 | * | 12/2003 | De Antoni Migliorati .................. B65B 39/005 141/286 |

(Continued)

FOREIGN PATENT DOCUMENTS

WO           200710365 A2      9/2007

*Primary Examiner* — Timothy L Maust
*Assistant Examiner* — James R Hakomaki
(74) *Attorney, Agent, or Firm* — The Small Patent Law Group LLC; Dean D. Small

(57) ABSTRACT

A filler adaptor assembly includes a base, an outer ring, and iris members. The base has a central opening. The outer ring is disposed circumferentially about the base and is rotatable relative to the base. The iris members are pivotably coupled to the base. The iris members cooperate to define an iris opening and are movable to vary the iris opening. The iris members are coupled to the outer ring, and move between an open position and a closed position when the outer ring is rotated relative to the base.

18 Claims, 10 Drawing Sheets

(56) References Cited

U.S. PATENT DOCUMENTS

| | | | |
|---|---|---|---|
| 6,796,328 B2* | 9/2004 | Myles | F16K 3/03 |
| | | | 137/557 |
| 6,929,041 B2 | 8/2005 | Falligant et al. | |
| 7,819,728 B2* | 10/2010 | Beckley | B60N 3/106 |
| | | | 454/155 |
| 7,886,783 B2* | 2/2011 | Rindy | A61M 16/183 |
| | | | 141/302 |
| 8,215,613 B2* | 7/2012 | Cheung | F16K 3/03 |
| | | | 251/212 |
| 8,727,303 B2* | 5/2014 | Araujo | E21B 33/061 |
| | | | 251/1.1 |
| 8,910,920 B1* | 12/2014 | Daniels | F16K 31/535 |
| | | | 251/212 |
| 10,287,841 B2* | 5/2019 | Zonoz | F04B 15/00 |
| 2011/0124873 A1* | 5/2011 | Hoge | C07F 9/46 |
| | | | 546/304 |
| 2011/0132905 A1* | 6/2011 | Ognjanovski | B60K 15/0406 |
| | | | 220/86.2 |
| 2013/0126464 A1* | 5/2013 | Manzke | B65B 3/04 |
| | | | 215/386 |
| 2016/0068064 A1* | 3/2016 | Park | B60K 15/05 |
| | | | 296/97.22 |

\* cited by examiner

SYSTEMS AND METHODS FOR BOTTLE RETENTION

BACKGROUND OF THE INVENTION

The subject matter disclosed herein relates generally to apparatus and methods for placing and/or retaining a bottle in a desired position. For example, various embodiments provide for bottle placement and retention for use with a vaporizer during a medical procedure (e.g., administration of an anesthetic agent).

To fill a vaporizer with an anesthetic agent, a bottle containing the agent may be inserted into a filler portion of the vaporizer. Certain conventional approaches require a number of steps or actions to be taken by a user, including rotation of a filler and/or bottle during insertion. Additionally, it may be noted that some anesthetic agents may produce pressure if there is a significant increase in temperature from either the environment or being warmed by contact with an operator's hands. However, certain conventional approaches require the bottle to be held by hand during filling.

BRIEF DESCRIPTION OF THE INVENTION

In one example embodiment, a filler adaptor assembly is provided that includes a base, an outer ring, and iris members. The base has a central opening. The outer ring is disposed circumferentially about the base and is rotatable relative to the base. The iris members are pivotably coupled to the base. The iris members cooperate to define an iris opening and are movable to vary the iris opening. The iris members are coupled to the outer ring, and move between an open position and a closed position when the outer ring is rotated relative to the base.

In another example embodiment, a vaporizer assembly is provided that includes a vaporizer and a filler adaptor assembly. The vaporizer includes a sleeve having a flange, mounting feature, and tube. The filler adaptor assembly is coupled to the sleeve, and includes a base, an outer ring, and iris members. The base is coupled to the mounting feature and has a central opening aligned with the tube of the sleeve. The outer ring is disposed circumferentially about the base and is rotatable relative to the base. The iris members are pivotably coupled to the base, and cooperate to define an iris opening. The iris members are movable to vary the iris opening. The iris members are coupled to the outer ring, and move between an open position and a closed position when the outer ring is rotated relative to the base.

In another example embodiment, a method is provided that includes inserting a leading end of a bottle into a central opening of a base of a filler adaptor assembly coupled to a vaporizer. The method also includes rotating an outer ring of the filler adaptor assembly with respect to the base to move iris members toward a closed position around a securement portion of the bottle. Further, the method includes urging the iris members against the securement portion of the bottle to maintain the bottle in position.

DETAILED DESCRIPTION OF THE INVENTION

Figure 1:
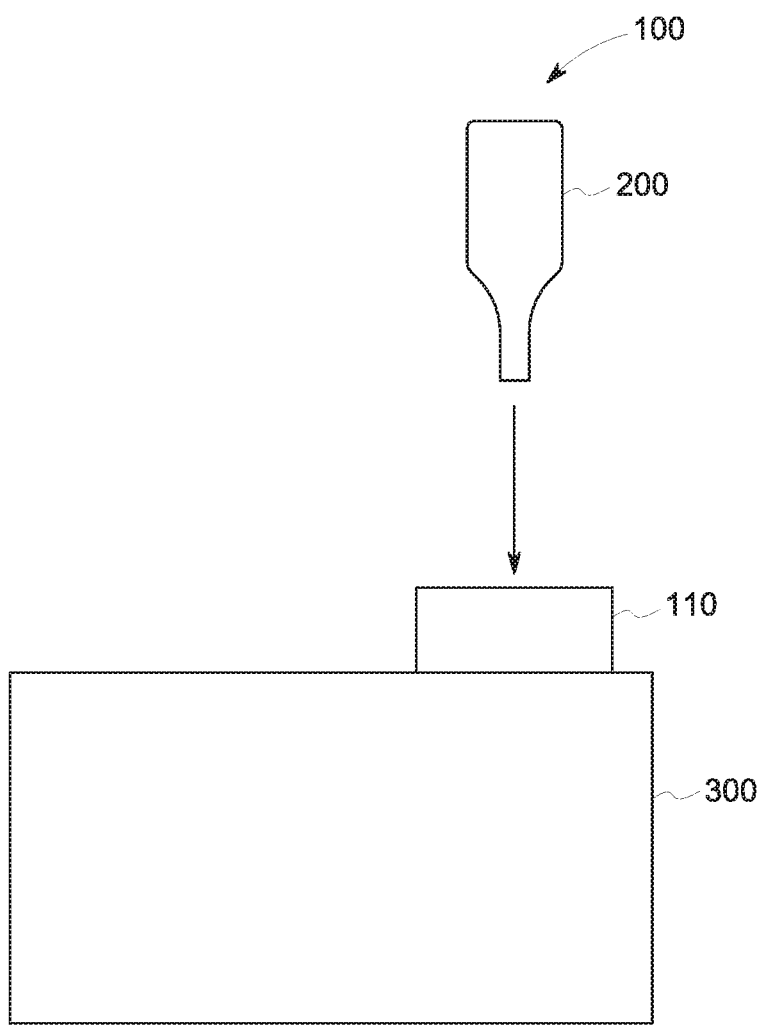
FIG. 1 provides a schematic block view of a vaporizer assembly in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware. It should be understood that the various embodiments are not limited to the arrangements and instrumentality shown in the drawings.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide improved placement and retention of bottles, for example in vaporizers for administration of an anesthetic agent. In various embodiments, the bottle is inserted into a stationary filler adaptor assembly by a simple, straight-in (e.g., no twisting of bottle required) insertion along an axis of the filler adaptor assembly. The filler adaptor assembly automatically allows the bottle to be secured in an operating position without requiring any action from an operator other than the straight-in insertion. In various embodiments, once the bottle is completely inserted, an iris mechanism of the filler adaptor assembly closes automatically (e.g., responsive to an urging toward a closed position by one or more springs) around a collar of the bottle to secure the bottle in place for use. Once filling of the vaporizer is complete and the bottle is to be removed, an outer ring or collar of the filler adaptor assembly may be rotated to open the iris mechanism to allow bottle removal. For example, an operator may rotate the collar or outer ring with one hand and remove the bottle with the other hand. Various embodiments utilize an iris mechanism that provides a plurality of contact points 360 degrees around a bottle end in contrast to certain conventional approaches that only provide 2 contact points 180 degrees apart.

Accordingly, various embodiments secure a bottle in place during filling of a vaporizer and avoid extra placement steps such as rotating of a bottle and filler as required by certain conventional approaches. Further, in various embodiments the bottle does not need to be manually held in position during filling.

A technical advantage of various embodiments includes improved performance of bottle retention adaptors (e.g., for use with vaporizers). A technical advantage of various embodiments includes improved cost and/or time efficiency due to elimination of a rotating filler and associated costs. A technical advantage of various embodiments includes improved filling from a bottle, for example due to the elimination of requiring a user to manually hold the bottle in position.

FIG. 1 provides a schematic block view of a vaporizer assembly 100 in assembly 100 in accordance with various embodiments. The depicted vaporizer assembly 100 includes a filler adaptor assembly 110, a bottle 200, and a vaporizer 300. Generally, the bottle 200 is used to provide a substance (e.g., an anesthesia agent) to vaporizer 300 for use during a medical procedure. The filler adaptor assembly 110 is used to removably couple the bottle 200 to the vaporizer 300. As discussed herein, the filler adaptor assembly 110 in various embodiments is configured to improve the ease and/or reliability of coupling the bottle 200 to the vaporizer 300 and/or to improve the ease and/or reliability of removing the bottle 200 from the vaporizer 300.

Figure 2:
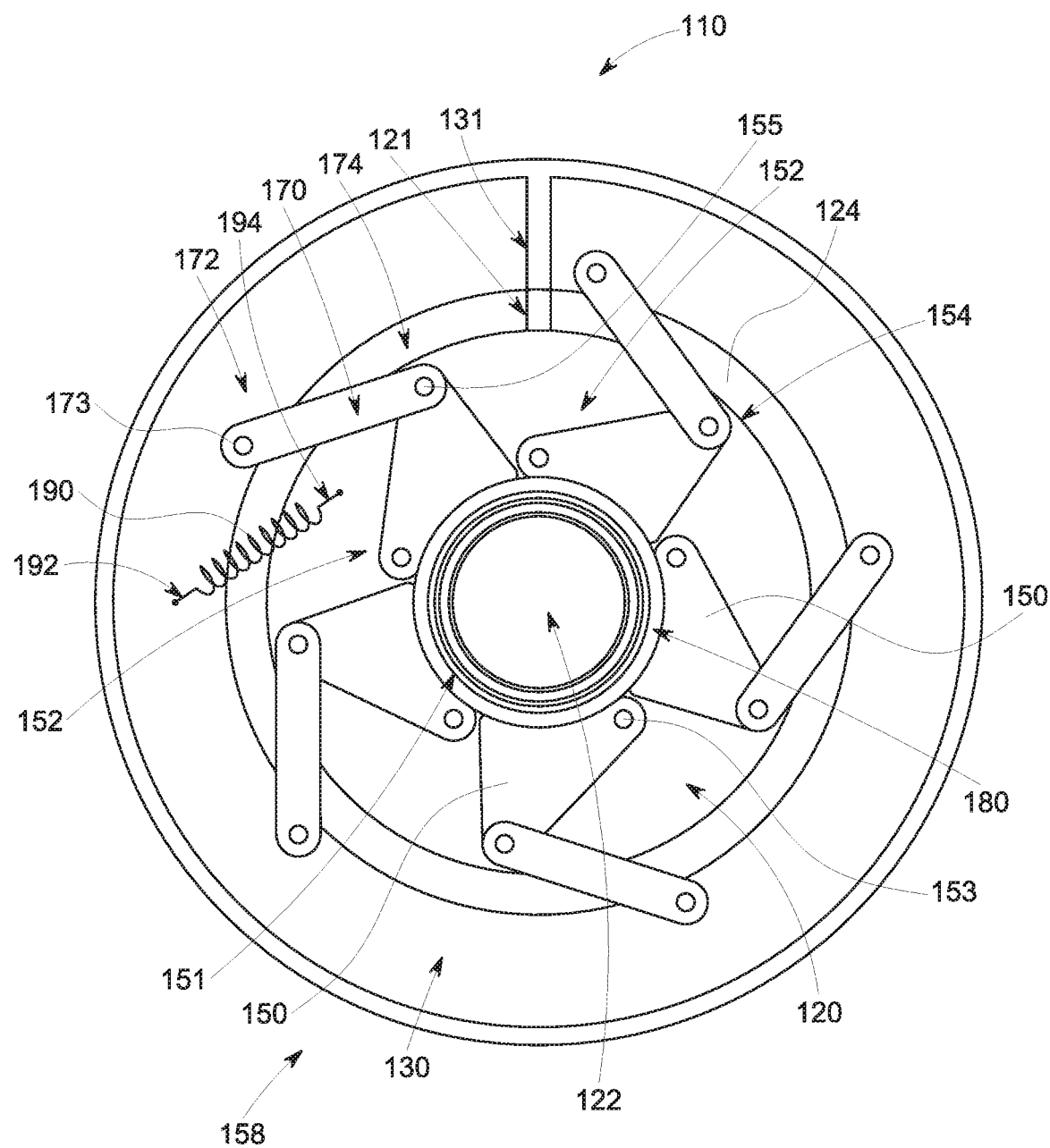
FIG. 2 provides a plan view of a filler adaptor assembly in an open position in accordance with various embodiments.
Figure 3:
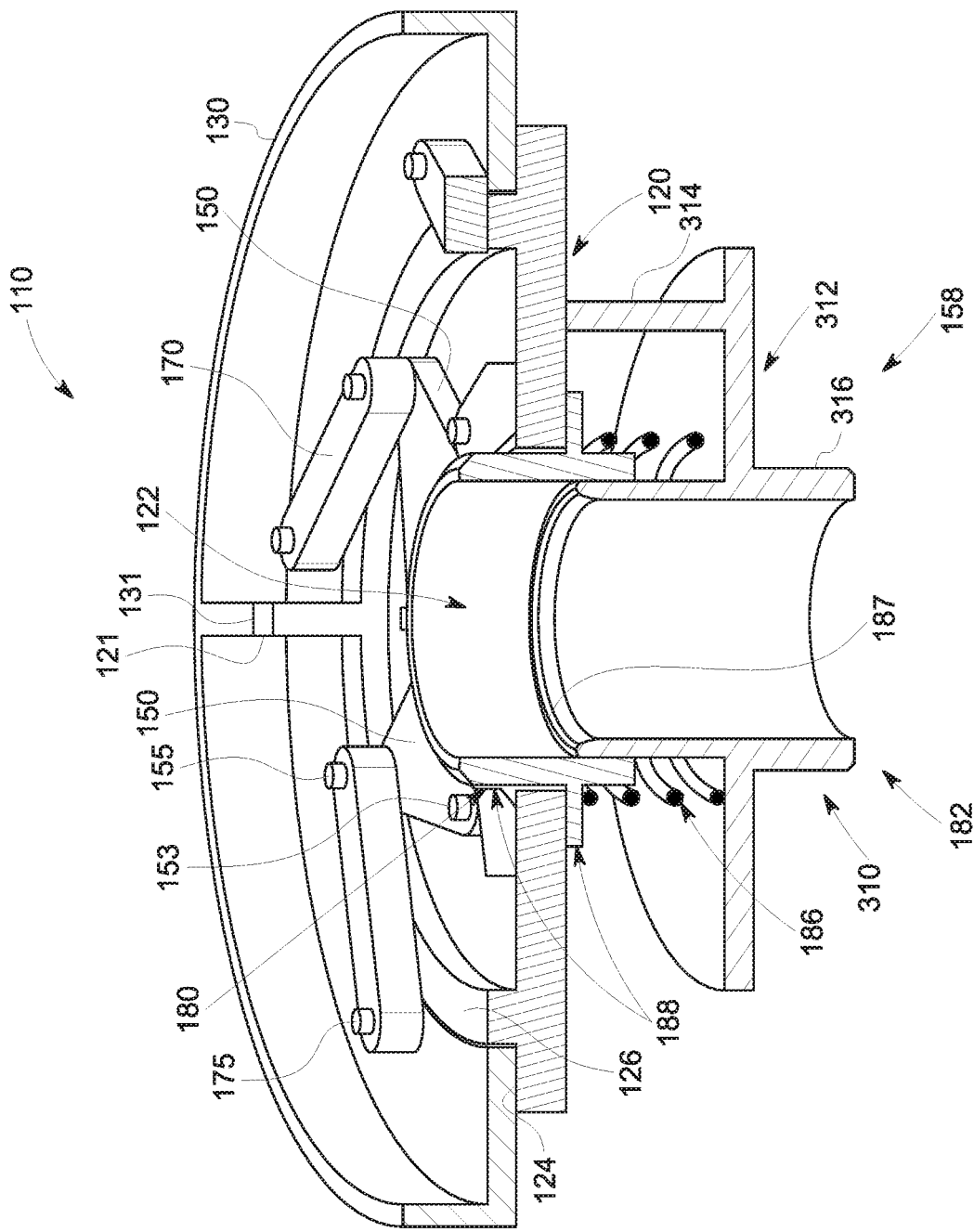
FIG. 3 provides a side perspective sectional view of the filler adaptor assembly of FIG. 2 in the open position.
Figure 4:
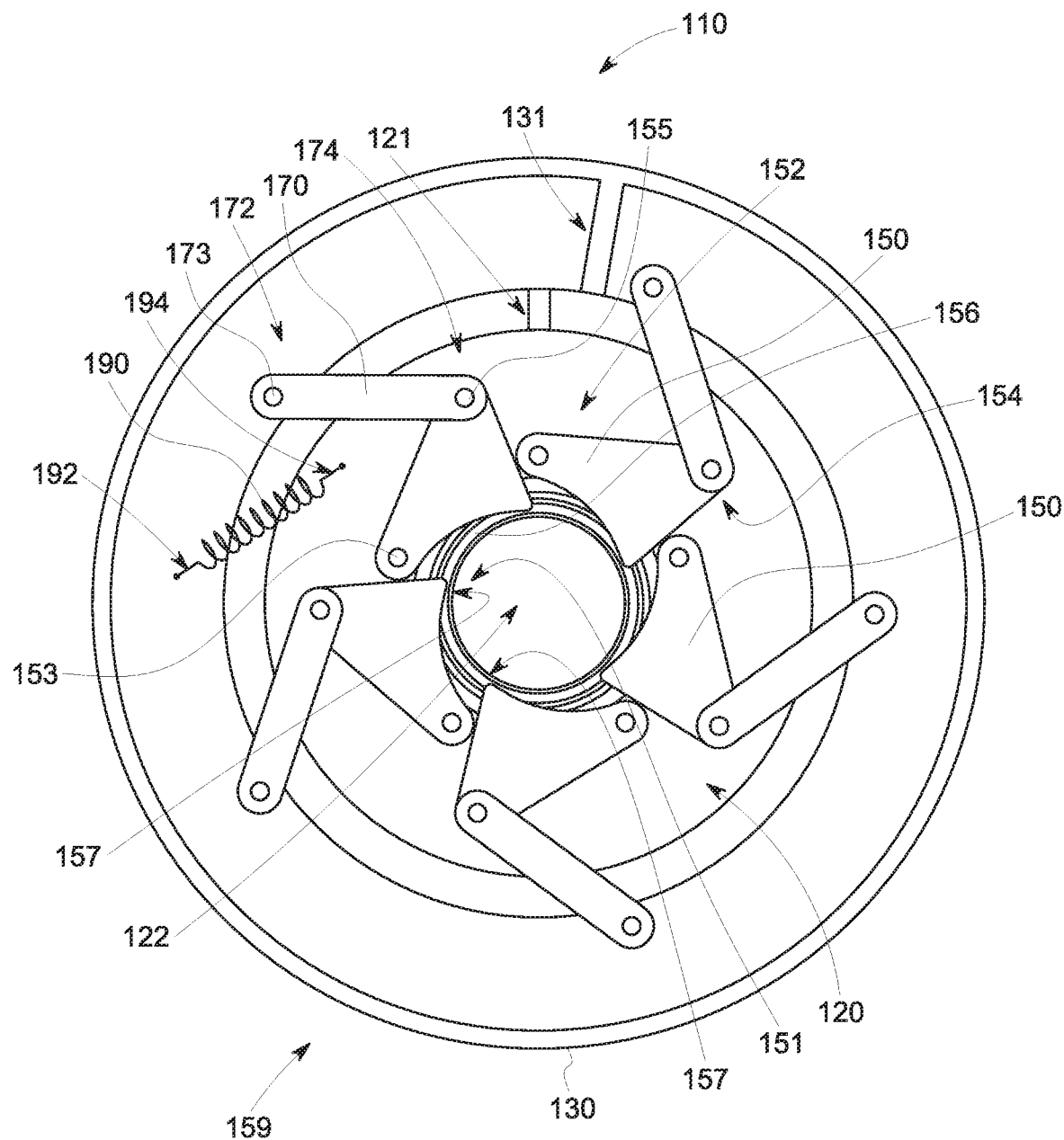
FIG. 4 provides a plan view of the filler adaptor assembly of FIG. 2 in a closed position.
Figure 5:
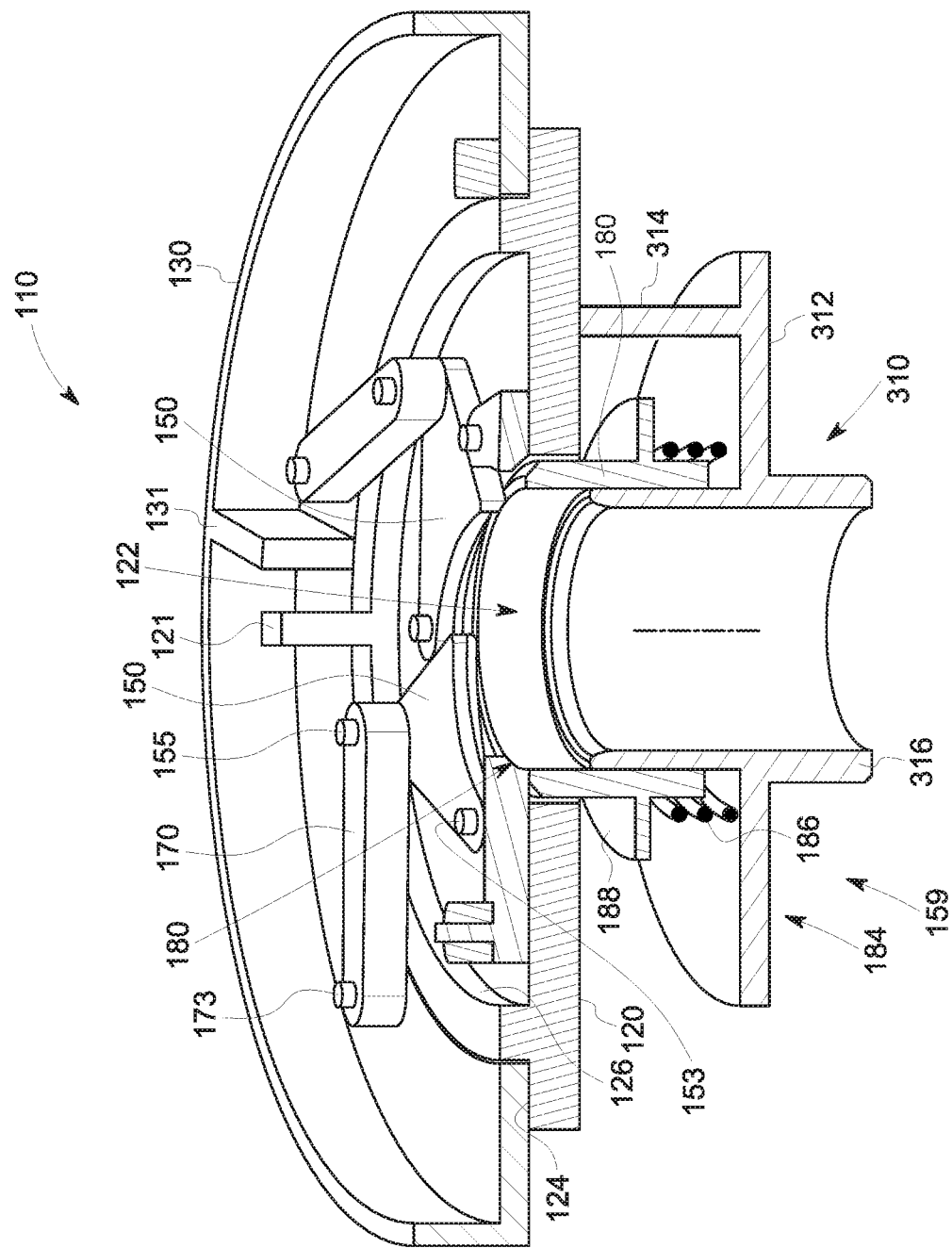
FIG. 5 provides a side perspective sectional view of the filler adaptor assembly of FIG. 2 in the closed position.

FIGS. 2-5 provide various views of an example filler adaptor assembly assembly 110 in accordance with various embodiments. FIG. 2 provides a plan view of the filler adaptor assembly 110 in an open position, and FIG. 3 provides a side perspective sectional view of the filler adaptor assembly 110 in the open position. FIG. 4 provides a plan view of the filler adaptor assembly 110 in a closed position, and FIG. 5 provides a side perspective sectional view of the filler adaptor assembly 110 in the closed position. It may be noted that the bottle 200 is not shown in FIGS. 2-5 for improved clarity of depiction of various components of the filler adaptor assembly 110.

As seen in FIGS. 2-5, the depicted filler adaptor assembly 110 includes a base 120, an outer ring 130, and iris members 150. Generally, the outer ring 130 is movable with respect to the base 120, and is used to actuate the iris members 150 between the open position (FIGS. 2 and 3) and the closed position (FIGS. 4 and 5). For example, the iris members 150 may be moved to the open position (and/or maintained in the open position) for insertion or removal of the bottle 200, and moved to the closed position (and/or maintained in the closed position) for securing the bottle 200 to the vaporizer 300 during use. It may be noted that the movement of the outer ring 130 with respect to the base 120 may be automatic or autonomous and/or performed manually. For example, the outer ring 130 in the illustrated embodiment is configured to rotate clockwise with respect to the base 120 automatically or autonomously (e.g., without an operator manipulating the outer ring), and to be rotated counter-clockwise with respect to the base 120 by an operator.

The depicted base 120 includes a central opening 122. The central opening 122 is sized to allow at least a portion of the bottle 200 to pass therethrough. In the illustrated example, the base 120 is generally configured as an annular ring disposed about the central opening 122. In various embodiments, the base 120 includes various features (e.g., pins, grooves, slots, guides, or the like) used for coupling to various components (e.g., iris members 150, outer ring 130) and/or to guide movement of various components. Generally, the base 120 is configured to be mounted to the vaporizer 300 either removably or permanently.

For example, as best seen in FIGS. 3 and 5, the vaporizer 300 includes a sleeve 310 that includes a flange 312, mounting feature 314, and tube 316. The tube 316 extends through the flange 312 and into the vaporizer 300. The bottle 200 in various embodiments is aligned by the filler adaptor assembly 110 with the tube 316 so that material from the bottle 200 enters the vaporizer 300 via the tube 316. The mounting feature 314 (which is depicted as a post in the illustrated example) is used for securing the base 120 to the sleeve 310. It may be noted that only one mounting feature 314 is shown in FIGS. 3 and 5; however, additional posts or other mounting features may be used in various embodiments.

With continued reference to FIGS. 2-5, the depicted outer ring 130 is disposed circumferentially about the base 120, and is rotatable relative to the base 120. In the illustrated embodiment, the outer ring 130 is configured as an annular ring that is disposed above the base 120 (with the vaporizer 300 understood as being disposed below the base 120) and partially overlaps the base 120 in a radial direction with the central opening 122 defining the origin of the radial direction. In the illustrated embodiment, the base 120 includes a ledge 124 and a shoulder 126, with the outer ring 130 disposed on the ledge 124 radially outward of shoulder 126. The ledge 124 and shoulder 126 cooperate to guide the outer ring 130 as the outer ring rotates with respect to the base 120. It may be noted that in various embodiments the outer ring 130 need not be radially outward of a shoulder. For example, the outer ring may be radially inward of a shoulder, or, as another example, a shoulder riding in a circular slot may be used to guide the outer ring. In the illustrated embodiment, alignment tabs (namely a base tab 121 and an outer ring tab 131) are depicted for visual clarity to help illustrate relative movement between the open position depicted in FIGS. 2 and 3 and the closed position depicted in FIGS. 4 and 5.

The depicted iris members 150 are pivotably coupled to the base 120, and cooperate to define an iris opening 151. The iris members 150 are movable (e.g., by pivoting with respect to the base 120) to vary the iris opening 151. In the illustrated example, the iris members are coupled to the outer ring 130, and move between an open position 158 (shown in FIGS. 2 and 3) and a closed position 159 (shown in FIGS. 4 and 5). In the open position 158, inner curved surfaces 156 of the iris members 150 cooperate to form a generally circular iris opening 151. In the closed position 159, the iris members 150 are individually pivoted with respect to the base 120 so that points of contact 157 of the iris members 150 move radially inward toward the center of the central opening 122 of the base 120 to grasp and secure the bottle 200 (the bottle 200 is not shown in FIGS. 2-5). It may be noted that the movement or pivoting of the iris members 150 may be continuous or non-stepped, so that various intermediate closed positions may be utilized to allow grasping and securing of bottles having various diameters. Generally, in various embodiments, a plurality of iris members 150 are utilized. For example, in the illustrated embodiment, five iris members 150 (with each corresponding to about 72 degrees of the circle defined in the open position) are utilized. However, it may be noted that more iris members 150 or fewer iris members 150 may be used in various embodiments.

As discussed above, the iris members 150 are coupled to the outer ring 130, and pivot with respect to the base 120 responsive to movement (e.g., rotation) by the outer ring 130 with respect to the base 120. It may be noted that the iris members 150 may be coupled directly or indirectly to the base 120 and/or the outer ring 130. For example, in the illustrated example, the iris members 150 are directly coupled to the base 120 (e.g., via pins 153), but indirectly coupled to the outer ring 130 via links 170. The depicted filler adaptor assembly 110 includes links 170 mounted to the outer ring 130, with each link 170 interposed between a corresponding iris member 150 and the outer ring 130 and coupling the corresponding iris member 150 to the outer ring 130. Rotating the outer ring 130 in a given direction causes movement of the links 170 which actuate the corresponding iris members 150 to pivot (e.g., about pins 153) to vary the size of the iris opening 151 (e.g., move the iris members toward the open or closed position).

In the illustrated embodiment, each link 170 has a first end 172 and a second end 174. The first end 172 of each link 170 is pivotally coupled to the outer ring 130 (e.g., via a corresponding pin 173). Also, the second end 174 of each link 170 is pivotally coupled to the corresponding iris member 150 (e.g., via a corresponding pin 155). It may be noted that each pin discussed herein may be configured as a post extending from one of the outer ring 130, base 120, link 170, or iris member 150 that is accepted by an opening on a corresponding component.

Each depicted iris member 150 includes a first portion 152, second portion 154, and inner curved surface 156. The first portion 152 of each iris member is pivotally coupled to the base 120 (e.g., via corresponding pin 153), and the second portion 154 is pivotally coupled to the second end 174 of the corresponding link 170 (e.g., via corresponding pin 175). The inner curved surface 156 of each iris member 150 is configured to cooperate with the inner curved surface 156 of the other iris members 150 to define the iris opening 151. For example, in the depicted open position (FIGS. 2 and 3) the inner curved surfaces 156 may cooperate to form a generally smooth circular shaped iris opening 151, whereas in the depicted closed position (FIGS. 4 and 5) portions of the inner curved surface 156 (e.g., points of contact 157) cooperate to form a reduced iris opening 151.

In various embodiments, the filler adaptor assembly 110 is configured to automatically or autonomously urge the outer ring 130 to rotate in a direction causing the iris members 150 to move toward the closed position. For example, the outer ring 130 in the illustrated embodiment is configured to autonomously or automatically rotate clockwise with respect to the base 120. The depicted filler adaptor assembly 110 includes an outer ring spring 190 that is coupled to the outer ring 130 and the base 120. The outer ring spring 190 is configured to urge the outer ring 130 to rotate with respect to the base 120 to move the iris members 150 toward the closed position. For example, the depicted outer ring spring 190 is configured as a linear spring having a first end 192 coupled to the outer ring 130 and a second end 194 coupled to the base 120, with the linear spring stretched in the position shown, so that the spring force of the linear spring urges the outer ring 130 in a clockwise direction. In other embodiments, additional linear springs may be used, and/or one or more torsional springs may be used to urge the outer ring 130 to move in a direction actuating the iris members 150 toward the closed position.

As best seen in FIGS. 3 and 5, the depicted filler adaptor assembly 110 includes a plunger 180. The plunger 180 is configured to be moved between an engaged position 182 (shown in FIG. 3) and a disengaged position 184 (shown in FIG. 5). When in the engaged position 182, the plunger 180 is disposed within the iris opening 151 to maintain the iris members 150 in the open position. However, when in the disengaged position 184, the plunger 180 is not disposed within the iris opening 151 (e.g., is at an elevation below the iris opening 151) to allow the iris members 150 to move or contract toward the closed position. Accordingly, when the plunger 180 is moved to the disengaged position 184, the iris members 150 may move toward the closed position due to the urging of the outer ring 130 in the clockwise direction by the outer ring spring 190 in the illustrated embodiment. However, when the plunger 180 is in the engaged position 182, the plunger 180 acts to restrict the iris members 150 from moving further radially inward.

In various embodiments, the filler adaptor assembly 110 includes a plunger spring 186 that is coupled to the plunger 180 and is configured to urge the plunger 180 toward the engaged position. For example, in the illustrated embodiment, the plunger 180 is configured as a tubular stem 187 with a plunger flange 188 extending radially outward from the tubular stem 187. The stem 187 is sized to slide over the tube 316 of the sleeve 310 of the vaporizer. The plunger spring 186 is coupled to the plunger 180 and the flange 312 of the sleeve 310 of the vaporizer 300. For example, the depicted plunger spring 186 is a coiled spring radially disposed about the stem 187 and tube 316, and compressed between the plunger flange 188 and the flange 312 of the sleeve 310 to urge the plunger 180 away from the vaporizer and toward the engaged position. When fully in the engaged position, the plunger flange 188 contacts and is restricted from further movement by a lower surface of the base 120. Accordingly, the plunger spring 186 provides for automatic or autonomous movement of the plunger 180 to the engaged position when not subject to an exterior force (e.g., upon removal of bottle 200 from the filler adaptor assembly 110.

Figure 6:
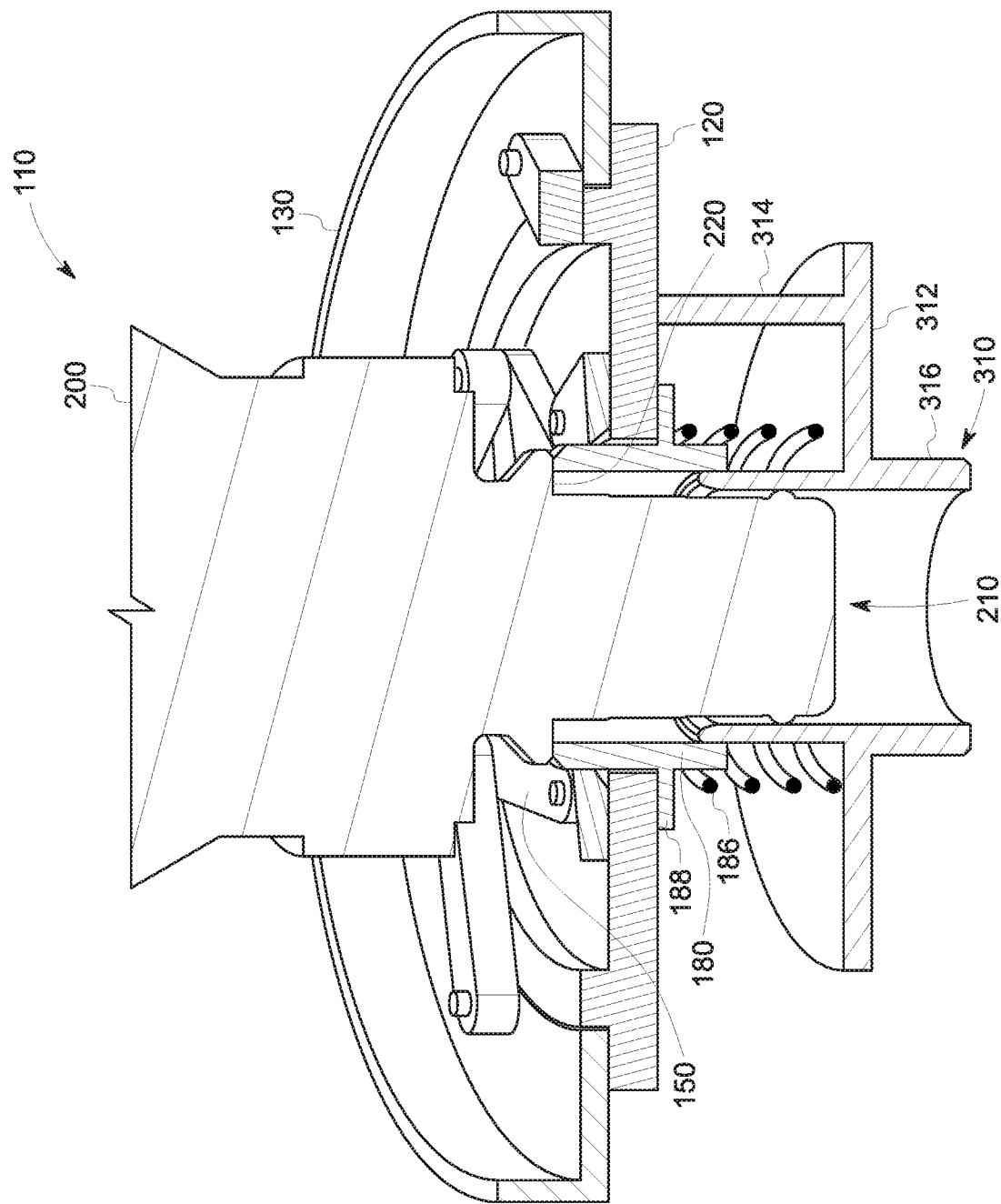
FIG. 6 provides a side sectional view of a bottle being inserted into the filler adaptor assembly of FIG. 2.
Figure 7:
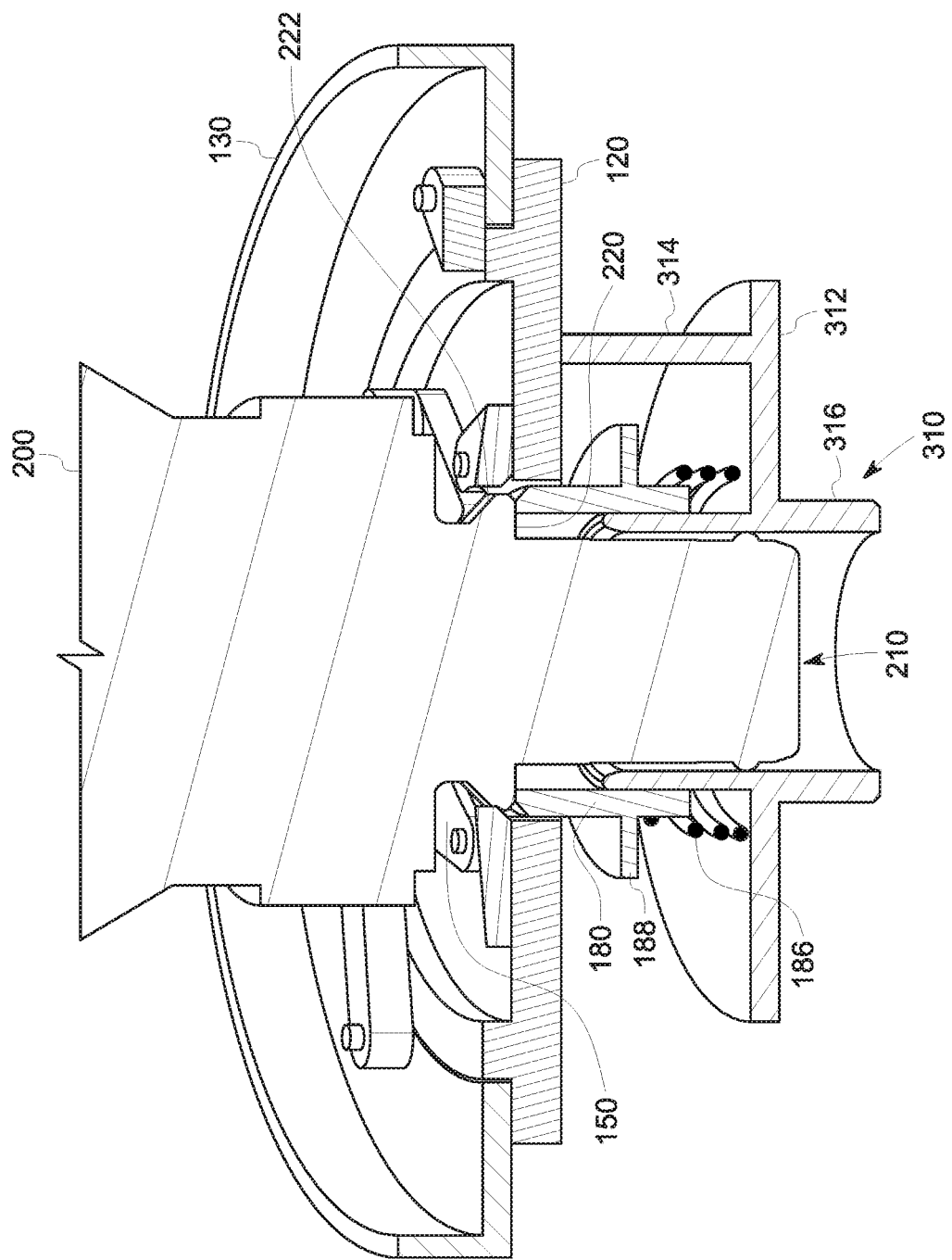
FIG. 7 provides a side sectional view of a bottle being inserted into the filler adaptor assembly of FIG. 2.
Figure 8:
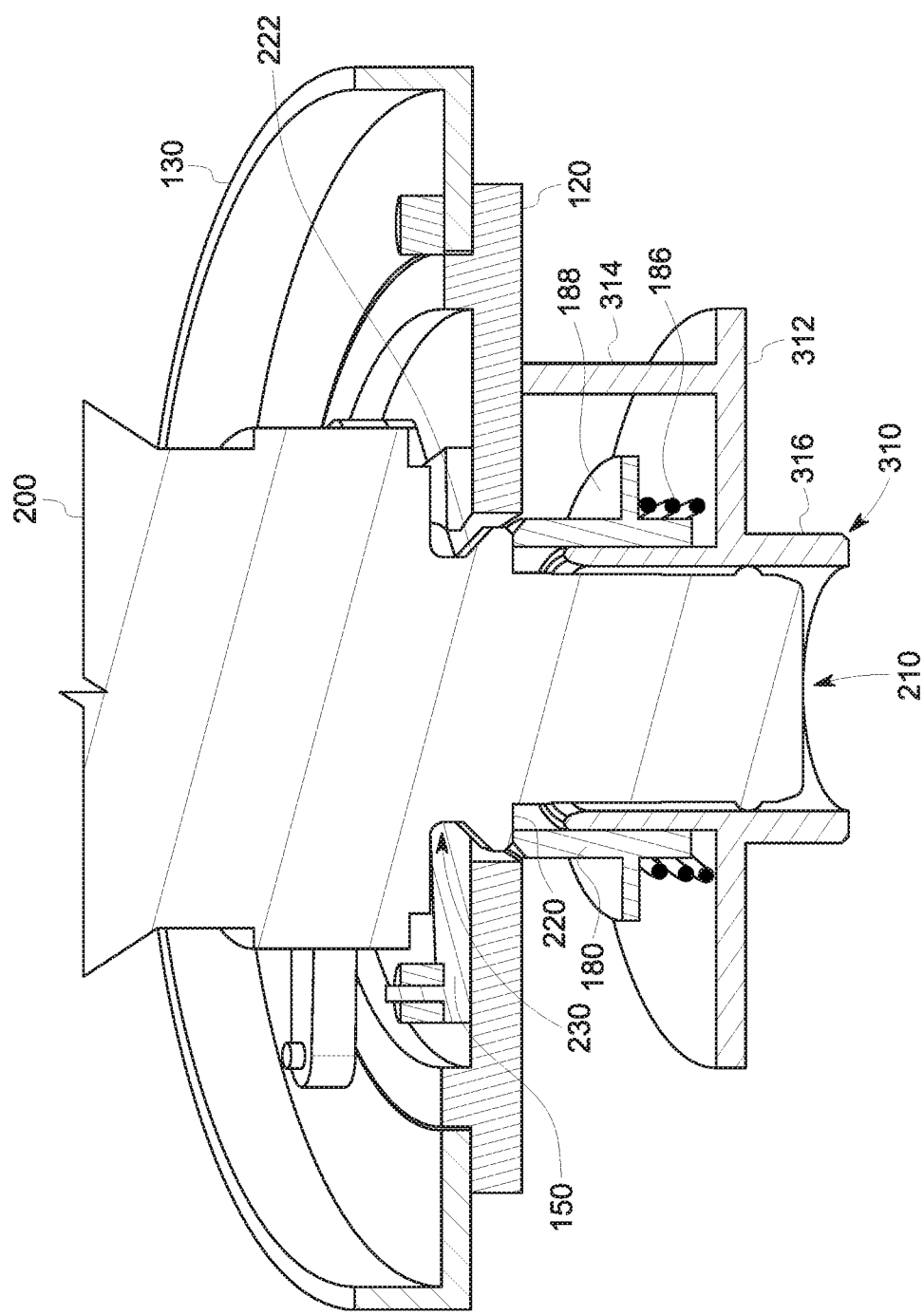
FIG. 8 provides a side sectional view of a bottle being inserted into the filler adaptor assembly of FIG. 2.

FIGS. 6-8 provide side sectional views of various stages of insertion of the bottle 200 into the filler adaptor assembly 110. For example, FIG. 6 provides a side sectional view of the bottle 200 inserted to a point where the bottle 200 first touches the plunger 180. The illustrated bottle 200 has a leading end 210 that is inserted into the tube 316 of the sleeve 310 of the vaporizer 300. As the leading end 210 is inserted into the tube 316, a bottle flange 220 of the bottle 200 contacts the plunger 180, as shown in FIG. 6. In this position, the plunger 180 is still in the engaged position, and maintained in the engaged position by the plunger spring 186 urging the plunger upward. With the plunger 180 in the engaged position, the iris members 150 are maintained in the open position. As the bottle 200 is urged downward past the position depicted in FIG. 6, the plunger spring 186 is compressed and the plunger 180 moves toward the disengaged position.

FIG. 7 provides a side sectional view of the bottle 200 inserted to a point where iris members 150 may start moving radially inward toward the closed position. As seen in FIG. 7, the bottle 200 has been moved down far enough for the plunger 180 to be moved below the iris opening 151 by the bottle flange 220. At this point, the plunger 180 no longer restricts the radially inward movement of the iris members 150, and the iris member 150 start pivoting toward the closed position (e.g., due to the clockwise urging of the outer ring 130 by the outer ring spring 190). As the bottle 200 is pushed downward and the iris members 150 move toward the closed position, the iris member 150 contact a sloped surface 222 leading from the bottle flange 220 to a groove 230.

FIG. 8 provides a side sectional view of the bottle 200 at a fully inserted point. Here, the leading end 210 of bottle 200 is fully inserted to an operational depth in the tube 316, and the iris members 150 have moved to the closed position around the groove 230 of the bottle 200. In this position, the iris members 150 secure the bottle 200 in an operational position where the contents of the bottle 200 (e.g., an anesthetic agent) may be delivered to the vaporizer. It may be noted that the insertion process may be performed using a single hand and does not require twisting of the bottle 200, or alignment of any particular feature along the circumference of the bottle 200 with a corresponding feature of the vaporizer 300, thereby providing convenient, reliable, easy one-handed insertion of the bottle 200. For removal, the bottle 200 may be pulled upward (e.g., after moving the iris members 150 to the open position by manually rotating the outer ring 130 with respect to the base 120). As the bottle 200 moves upward, the iris members 150 are gradually moved toward the open position against the sloped surface 222. At the same time, the plunger spring 186 urges the plunger 180 upward with the receding bottle 200. Eventually, as the iris members 150 continue to be forced open by the sloped surface 222, the plunger 180 reaches the engaged position, restricting the iris members 150 to the open position, allowing insertion of another bottle 200 for the next use of the vaporizer 300.

Figure 9:
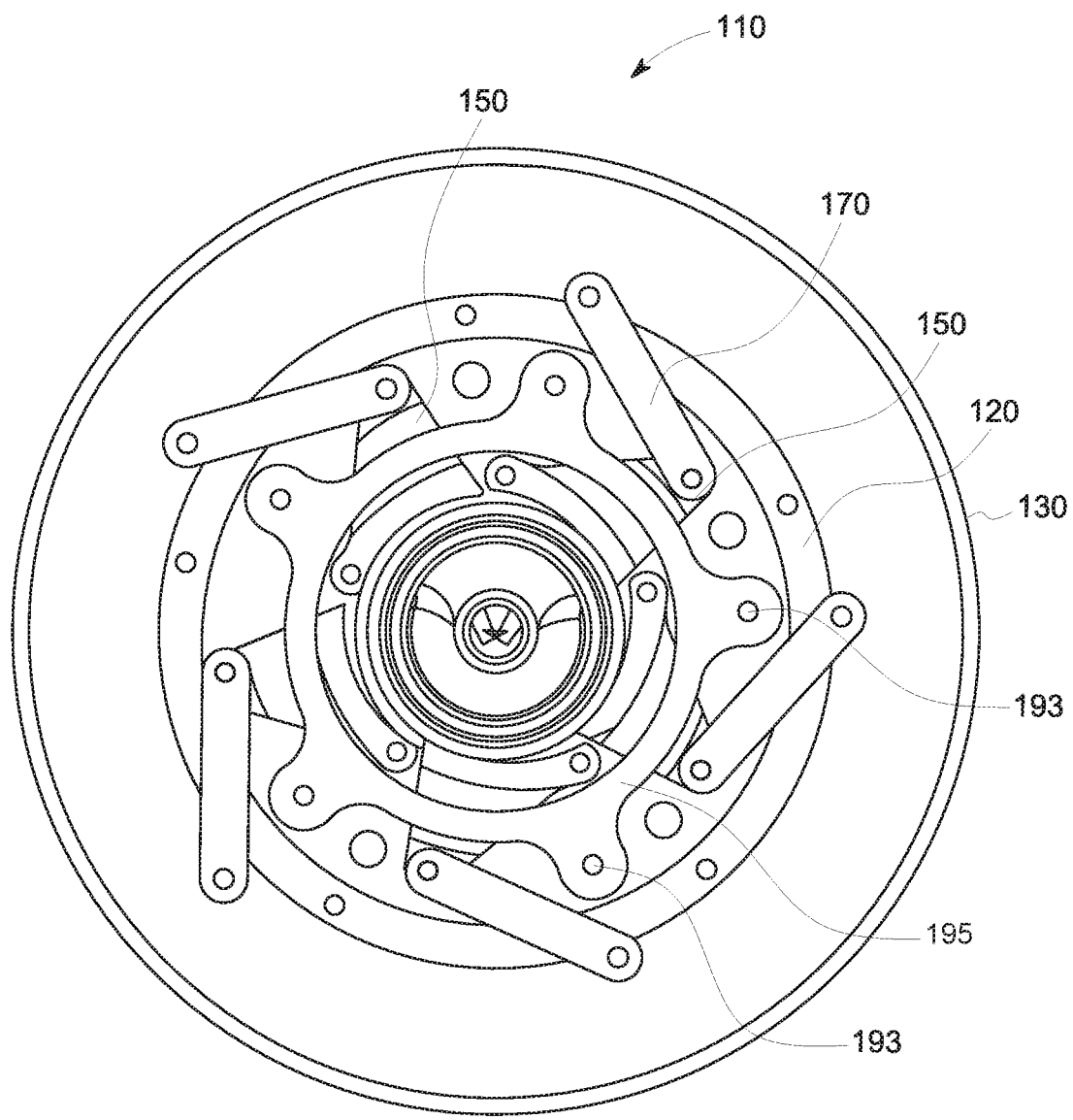
FIG. 9 provides a plan view of a filler adaptor assembly that includes an iris retainer in accordance with various embodiments.

It may be noted that the iris members 150 may be subject to cocking or twisting forces that may tend to urge the iris members 150 to move otherwise than parallel along the base 120. Accordingly, in various embodiments, the filler adaptor assembly 110 includes an iris retainer 195. FIG. 9 provides a plan view of the filler adaptor assembly 110 including an iris retainer 195. The depicted iris retainer 195 is coupled to the base 120 (e.g., via pins 193) with the iris members 150 interposed between the iris retainer 195 and the base 120. Accordingly, with the iris retainer 195 above the iris members 150 and the base 120 below the iris members 150, any cocking of the iris members 150 is eliminated or reduced, and the movement of the iris members 150 is guided along a path generally parallel to the upper surface of the base 120.

Figure 10:
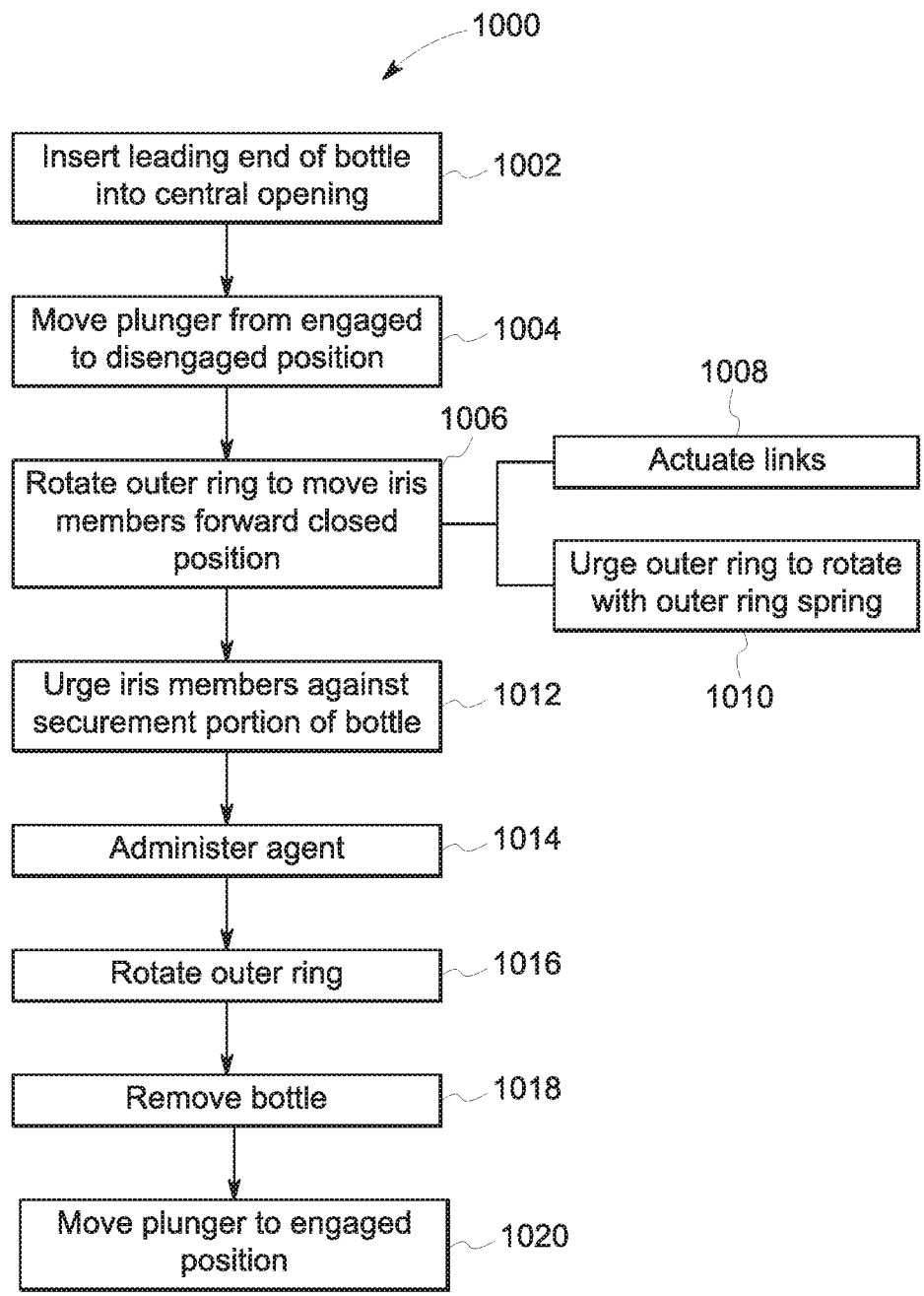
FIG. 10 provides a flowchart of a method in accordance with various embodiments.

FIG. 10 provides a flowchart of a method 1000 (e.g., for inserting and/or removing a bottle from a vaporizer), in accordance with various embodiments. The method 1000, for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion.

At 1002, a leading end of a bottle (e.g., bottle 200) is inserted into a central opening of a base (e.g., base 120) of a filler adaptor assembly (e.g., filler adaptor assembly 110) coupled to a vaporizer (e.g., vaporizer 300). The bottle in various examples includes an anesthetic agent to be administered to a patient via the vaporizer. Generally, the filler adaptor assembly is configured to position and secure the bottle. For example, in various embodiments, as discussed herein, the filler adaptor assembly includes members that articulate to vary an opening size for securing the bottle when the bottle is inserted.

In the illustrated example, at 1004, a plunger (e.g., plunger 180) is moved from an engaged position to a disengaged position while the leading end of the bottle is inserted into the central opening of the base. For example, the bottle may include a flange (e.g., bottle flange 220) or other feature configured to contact the plunger while the bottle is being inserted and move the plunger along with the bottle as the bottle is further inserted.

At 1006, an outer ring (e.g., outer ring 130) of the filler adaptor assembly is rotated with respect to the base to move iris members (e.g., iris members 150) toward a closed position around a securement portion (e.g., groove 230). It may be noted that in various embodiments the rotation of the outer ring may occur while the bottle is being inserted, and also may overlap in time at least partially with the movement of the plunger at 1004.

It may be noted that the outer ring may be indirectly coupled to the iris members (e.g., with one or more structures interposed between the outer ring and a given iris member and coupled to both the outer ring and the given iris member). For example, in the illustrated embodiment, at 1008, rotating the outer ring of the filler adaptor assembly actuates links (e.g., links 170) that are coupled to the iris members to move the iris members toward the closed position.

In some embodiments, the rotation of the outer ring may occur automatically in response to the movement of the plunger to the disengaged position. For example, in the illustrated embodiment, at 1010, an outer ring spring (e.g., outer ring spring 190) is utilized to urge the outer ring to rotate with respect to the base . . . 1006 can happen while bottle is being inserted. Accordingly, for convenient automatic movement toward the closed position, in various embodiments a spring may be used to urge the filler adaptor assembly toward the closed position, with the spring overcome by a manually applied force (e.g., removal of the bottle) when it is desired to move the iris members toward the open position.

With the bottle fully inserted, at 1012, the iris members are urged against the securement portion of the bottle, maintaining the bottle in position to deliver contents of the bottle to the vaporizer. At 1014, an anesthetic agent is administered to the patient from the bottle via the vaporizer.

Once a procedure is complete and/or the bottle is empty, the bottle may be disengaged from the filler adaptor assembly and vaporizer. In the illustrated embodiment, at 1016, the outer ring is manually rotated with respect to the base to urge the iris members toward the open position. At 1018, with the iris members in the open position, the bottle is removed from the central opening of the base. At 1020, as the bottle is removed, the plunger is moved to an engaged position. The plunger maintains the iris members in the open position while the plunger is in the engaged position. For example, a plunger spring may act to automatically urge the plunger toward the engaged position when the bottle is removed. With the iris members in the open position, a new bottle may be inserted into the filler adaptor assembly for use with the vaporizer.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A filler adaptor assembly comprising:
    a base having a central opening;
    an outer ring disposed circumferentially about the base and rotatable relative to the base;
    iris members pivotably coupled to the base, the iris members cooperating to define an iris opening and movable to vary the iris opening, the iris members coupled to the outer ring wherein the iris members move between an open position and a closed position when the outer ring is rotated relative to the base; and
    a plunger configured to be moved between an engaged and disengaged position, wherein the plunger is disposed within the iris opening in the engaged position to maintain the iris members in the open position, and wherein the plunger is not disposed within the iris opening in the disengaged position to allow the iris members to move toward the closed position.

2. The filler adaptor assembly of claim 1, further comprising:
    links mounted to the outer ring, each link coupling a corresponding iris member to the outer ring.

3. The filler adaptor assembly of claim 2, wherein each link has a first end pivotally coupled to the outer ring and a second end pivotally coupled to the corresponding iris member.

4. The filler adaptor assembly of claim 3, wherein each iris member has a first portion pivotally coupled to the base, a second portion pivotally coupled to the second end of the corresponding link, and an inner curved surface configured to cooperate with inner curved surfaces of other iris members to define the iris opening.

5. The filler adaptor assembly of claim 1, further comprising an outer ring spring coupled to the outer ring and the base, the outer ring spring configured to urge the outer ring to rotate with respect to the base to move the iris members toward the closed position.

6. The filler adaptor assembly of claim 1, further comprising a plunger spring coupled to the plunger and configured to urge the plunger toward the engaged position.

7. The filler adaptor assembly of claim 6, further comprising an iris retainer coupled to the base, the iris members interposed between the iris retainer and the base.

8. A method comprising:
    inserting a leading end of a bottle into a central opening of a base of a filler adaptor assembly coupled to a vaporizer;
    rotating an outer ring of the filler adaptor assembly with respect to the base to move iris members toward a closed position around a securement portion of the bottle; and
    urging the iris members against the securement portion of the bottle to maintain the bottle in position; and
    moving a plunger to an engaged position while removing the bottle, wherein the plunger maintains the iris members in the open position while the plunger is in the engaged position.

9. The method of claim 8, wherein rotating the outer ring of the filler adaptor assembly actuates links coupled to the iris members to move the iris members toward the closed position.

10. The method of claim 8, wherein urging the iris members against the securement portion of the bottle comprises utilizing an outer ring spring to urge the outer ring to rotate with respect to the base.

11. The method of claim 8, further comprising moving the plunger from the engaged position to a disengaged position while inserting the leading end of the bottle into the central opening of the base.

12. The method of claim 8, further comprising manually rotating the outer ring with respect to the base to urge the iris members toward the open position, and removing the bottle from the central opening of the base.

13. A vaporizer assembly comprising:
    a vaporizer comprising a sleeve having a flange, mounting feature, and tube; and
    a filler adaptor assembly coupled to the sleeve, the filler adaptor comprising:
        a base coupled to the mounting feature and having a central opening aligned with the tube of the sleeve;
        an outer ring disposed circumferentially about the base and rotatable relative to the base; and
        iris members pivotably coupled to the base, the iris members cooperating to define an iris opening and movable to vary the iris opening, the iris members coupled to the outer ring wherein the iris members move between an open position and a closed position when the outer ring is rotated relative to the base.

14. The vaporizer assembly of claim 13, further comprising:
    links mounted to the outer ring, each link coupling a corresponding iris member to the outer ring.

15. The vaporizer assembly of claim 14, wherein each link has a first end pivotally coupled to the outer ring and a second end pivotally coupled to the corresponding iris member.

16. The vaporizer assembly of claim 15, wherein each iris member has a first portion pivotally coupled to the base, a second portion pivotally coupled to the second end of the corresponding link, and an inner curved surface configured to cooperate with the inner curved surface of other iris members to define the iris opening.

17. The vaporizer assembly of claim 13, further comprising a plunger configured to be moved between an engaged and disengaged position, wherein the plunger is disposed within the iris opening in the engaged position to maintain the iris members in the open position, and wherein the plunger is not disposed within the iris opening in the disengaged position to allow the iris members to move toward the closed position.

18. The vaporizer assembly of claim 17, further comprising a plunger spring coupled to the plunger and the flange of sleeve, and configured to urge the plunger toward the engaged position.

* * * * *